United States Patent
Reiman (12)

(10) Patent No.: US 6,374,130 B1
(45) Date of Patent: Apr. 16, 2002

(54) METHODS FOR TRACKING THE PROGRESSION OF ALZHEIMER'S DISEASE IDENTIFYING TREATMENT USING TRANSGENIC MICE

(76) Inventor: Eric M. Reiman, 7240 E. Sunnyside Dr., Scottsdale, AR (US) 85260

( * ) Notice: Subject to any disclaimer, the term of this patent is extended or adjusted under 35 U.S.C. 154(b) by 0 days.

(21) Appl. No.: 09/544,659

(22) Filed: Apr. 6, 2000

Related U.S. Application Data

(60) Provisional application No. 60/128,029, filed on Apr. 6, 1999.

(51) Int. Cl.[7] .................................................. A61B 5/05
(52) U.S. Cl. ............................ 600/407; 800/3; 800/13; 800/18; 428/894; 435/325
(58) Field of Search ............................... 800/13, 3, 18; 435/172.3, 29, 354, 69.1, 325, 320.1, 252.3; 514/1; 536/23.1, 23.5; 128/894; 600/407

(56) References Cited

U.S. PATENT DOCUMENTS

| | | | |
|---|---|---|---|
| 5,612,486 A | 3/1997 | McConlogue et al. | 800/2 |
| 5,720,936 A | 2/1998 | Wadsworth et al. | 424/9.1 |
| 5,894,078 A | 4/1999 | Nalbantolu et al. | 800/2 |
| 5,986,054 A | * 11/1999 | St. George-Hyslop et al. | 530/350 |
| 6,037,521 A | 3/2000 | Sato et al. | 800/18 |
| 6,211,428 B1 | * 4/2001 | Singh et al. | 800/13 |
| 6,248,555 B1 | * 6/2001 | Tanzi et al. | 435/69.1 |

OTHER PUBLICATIONS

Author: Lendon et al. Title: Exploring the Etiology of Alzheimer Disease Using Molecular Genetics Date: Mar. 12, 1997 Pages: Seven (7).

Author: Curt D. Sigmund Title: Are Studies In Genetically Altered Mice Out of Control? Date: Jan. 6, 2000 Pages: Five (5).

* cited by examiner

Primary Examiner—Marvin M. Lateef
Assistant Examiner—Jeoyuh Lin
(74) Attorney, Agent, or Firm—Jordan M. Meschkow; Lowell W. Gresham; Meschkow & Gresham, P.L.C.

(57) ABSTRACT

A method of screening pharmaceutical drugs, gene therapies, vaccines, dietary supplements, behavioral and environmental therapies and other clinical treatments for potential efficacy in the treatment of Alzheimer's disease in humans. The method includes selecting transgenic mice that are genetically altered for Alzheimer's disease and using measurement and/or imaging techniques to determine the activity level of the posterior cingulate region of the brains of the mice after treatment. Based on these measurements and comparisons to a control group, the effectiveness of the treatment in arresting or reversing Alzheimer's disease in mice can be determined, and the treatment can be identified as a promising candidate for human trials.

20 Claims, 3 Drawing Sheets

METHODS FOR TRACKING THE PROGRESSION OF ALZHEIMER'S DISEASE IDENTIFYING TREATMENT USING TRANSGENIC MICE

CROSS-REFERENCE TO RELATED APPLICATION

This application claims the benefit of U.S. Provisional application Ser. No. 60/128,029 filed Apr. 6, 1999.

FIELD OF INVENTION

This invention utilizes imaging techniques and other methods to measure the activity in a specific region of the brain in genetically modified mice to provide an indicator of the progression of Alzheimer's disease; furthermore, it utilizes this indicator of Alzheimer's disease progression to identify treatments with the potential to halt the progression or prevent the onset of this disorder.

BACKGROUND OF INVENTION

Alzheimer's disease is the most common form of memory and thinking problems (i.e., "dementia") in older people. According to one community survey, Alzheimer's dementia affects about 10% of those over the age of 65 and almost half of those over the age of 85. As the average life span continues to increase, Alzheimer's disease is expected to take an increasing toll on affected persons, family caregivers, and the communities in which they live.

Little by little, Alzheimer's disease robs affected individuals of their memory, judgment, and reasoning, their ability to recognize objects and familiar faces, their language skills, and their ability to perform routine tasks. In the most severe stage of the illness, individuals may be bed-ridden, totally confused, unable to move around or communicate with others, and unable to control their bladder or bowel functions. Affected persons commonly die from the complications of infections, accidents, or malnutrition. Indeed, Alzheimer's disease is the fourth leading cause of death in the United States.

Alzheimer's disease takes an extraordinary toll on the affected person's family. Family caregivers commonly feel frustrated, helpless, and physically exhausted. Half of them become clinically depressed. Many must become impoverished before the affected person is eligible for long-term residential care.

The financial impact of Alzheimer's disease on the community continues to grow. Currently, it costs about $175,000 to care for each person with Alzheimer's dementia. By the time today's young adults grow old, there will be four times as many people over the age of 65, eight times as many people over the age of 85, and a smaller proportion of individuals in younger age groups who will be expected to provide care for those affected by Alzheimer's disease.

For all of these reasons, researchers must find ways to halt the progression and prevent the onset of this devastating disorder. Scientific discoveries in the last few years have raised the hope that researchers will find effective ways to treat and prevent Alzheimer's disease.

For instance, autopsy studies reveal several characteristic brain abnormalities (often called "histopathological features") in patients with Alzheimer's disease: plaques, tangles, and a loss of brain cells. Researchers have begun to characterize the cascade of molecular events that lead to plaques (e.g., the aggregation of an unusually long form of a protein called "β-amyloid"); they have begun to characterize the molecular events that lead to the formation of tangles (e.g., the binding of phosphate molecules to a protein called "tau"); and they have begun to characterize the cascade of molecular events that lead to a loss of brain cells called "neurons" and their connections called "synapses" (e.g., inflammation, oxidation, and over-excitation of brain cells). Treatments that target one or more of these molecular events might be able to halt the progression of Alzheimer's disease or even prevent the onset of Alzheimer's disease altogether.

Furthermore, researchers have identified specific genes that appear to account for about half of all Alzheimer's disease cases. Rare mutations of the amyloid precursor protein (known as "APP") gene on chromosome 21, the presenilin 1 gene on chromosome 14, and the presenilin 2 gene appear to account for about half of those individuals who develop a form of Alzheimer's disease that runs in families and leads to the onset of memory and thinking problems prior to the age of 60 ("early-onset"). In addition to these rare mutations, the apolipoprotein E (APOE) ε4 gene on chromosome 19 (found in about one-fourth of the population) increases the risk and hastens the onset of memory and thinking problems in about half of those who develop Alzheimer's dementia after the age of 60. As researchers determine how the products of these genes lead to the development of Alzheimer's disease, they will provide additional targets for treatments to halt the progression and prevent the onset of this disorder.

Finally, researchers have already identified clinical treatments that might slow the progression or delay the onset of Alzheimer's disease. Promising treatments include, but are not limited to, anti-oxidants like vitamin E, anti-inflammatory medications like indomethacin, estrogen replacement therapy, recently developed amyloid blocking agents, and a potential Alzheimer's disease vaccine. A treatment that delays the onset of Alzheimer's dementia by only 5 years has the potential to cut in half the number of new cases of this devastating disease.

Despite these promising observations, one of the greatest obstacles to the discovery of Alzheimer's disease treatments has been the absence of a marker of disease progression in laboratory animals. A marker of Alzheimer's disease progression in laboratory animals could be used to screen pharmaceutical compounds and other treatments for their ability to halt the progression and prevent the onset of this disorder. This screening procedure could identify promising treatments, give chemists direction in the refinement or new design of promising pharmaceutical compounds, and give the pharmaceutical industry direction in selecting which treatments to test in expensive and time-consuming clinical trials. Companies need to have confidence in a potential treatment before they are willing to spend the time, effort, and millions of dollars needed to establish its efficacy and safety and merit approval from the United States Food and Drug Administration (FDA).

Capitalizing on the discovery of specific genetic risk factors for Alzheimer's disease and refinements in genetic engineering, research groups have recently begun to produce strains of genetically modified mice that develop some of the characteristic brain abnormalities found at autopsy in persons with Alzheimer's dementia, such as amyloid plaques. For instance, some research groups have developed transgenic mice that over express abnormal forms of human APP found in certain families with early-onset Alzheimer's disease; some have developed transgenic mice that over express abnormal forms of the human presenilin 1 protein found in certain other families with early-onset Alzheimer's disease; some have developed transgenic mice that overexpress human the APOE ε4 protein found in many persons with late-onset Alzheimer's disease; and some have developed transgenic mice with a combination of genetic modifications (e.g., transgenic/knockout mice that contain a mutant form of the human APP transgene and the human APOE ε4 transgene and lack the mouse APOE gene). Researchers continue to work on the development of genetically modified mice that could serve as a laboratory model of Alzheimer's disease.

To date, the most promising animal models of Alzheimer's disease have been transgenic mice who overexpress abnormal forms of APP and develop amyloid plaques (e.g., the PDAPP mice first described by Dora Games and her colleagues). While these mice represent an important advance in the effort to find Alzheimer's disease treatments, uncertainties remain about the validity of these and other animal models and the best way to monitor disease progression in the absence of symptoms. First, transgenic mice generally lack some of the characteristic histopathological features of Alzheimer's disease, such as tangles and neuronal loss. Second, it remains possible that amyloid plaques are insufficient to account for the clinical features of Alzheimer's disease. Third, since amyloid is deposited in the early stages of Alzheimer's disease and does not progress during the course of the illness, plaque formation might constitute a more valuable marker of the pre-clinical and early clinical stages of Alzheimer's disease, than of the latter clinical stages. Finally, even though behavioral and electrophysiological evidence of memory impairment has been observed in at least one of the transgenic mouse lines, it is difficult to relate these observations to the clinical symptoms of Alzheimer's dementia, as experienced in humans.

Because it is difficult to assess symptoms in laboratory mice, researchers need to find a marker of Alzheimer's disease that bridges the gap between persons with the disorder and promising animal models. In accordance with the invention detailed below, brain imaging techniques provide the means to characterize the progression of Alzheimer's disease in animals in the absence of symptoms.

Functional brain imaging techniques, such as positron emission tomography (PET), provide information about the inner workings of the human brain. Measuring the uptake of a radioactive tracer called fluorodeoxyglucose (FDG) in the brain, PET provides information about the rates of glucose metabolism in different regions of the brain and, more generally, the activity of brain cells that project to those regions. PET studies find that persons with Alzheimer's disease have significant reductions in FDG uptake in certain regions of the brain, including posterior cingulate, parietal, temporal, and prefrontal cortex, which become more pronounced during the course of the illness. The largest reduction is in the posterior cingulate cortex, especially early in the course of the illness. This reduction becomes apparent prior to the onset of cognitive impairment in persons at genetic risk for the disorder, is correlated with the severity of cognitive impairment in persons with Alzheimer's dementia, and may provide the earliest marker of Alzheimer's disease progression (Reiman et al, *New Engl J Med*, 1996; Reiman et al, *Ann Neurol*, 1998; Reiman et al, *Flinn Foundation Biomed Res Life Sci Symposium* [abstract], 1998). While FDG uptake is preferentially reduced in the brain regions noted above, it is preferentially spared in certain other brain regions, including visual cortex, sensorimotor cortex, cerebellum, pons, and white matter regions-although there is a reduction in whole brain glucose metabolism during the latter stages of the illness. While the characteristic and progressive pattern of reductions in brain activity has been best studied using PET measurements of FDG uptake, this pattern has also been noted using other markers of regional brain activity, including, but not limited to, PET measurements of cerebral blood flow, single photon emission computed tomographic (SPECT) measurements of cerebral blood flow, magnetic resonance imaging measurements of cerebral blood flow and blood volume, and magnetic resonance spectroscopic measurements of N-acetyl aspartic acid.

SUMMARY OF THE INVENTION

The invention utilizes measurements of brain activity in posterior cingulate cortex as an indicator of Alzheimer's disease progression in mice engineered to contain a genetic risk factor for this disorder. The method provides the capacity to study factors that cause or influence the development of Alzheimer's disease. It provides the capacity to screen existing, modified, or newly developed pharmaceutical compounds and other clinical treatments for their ability to halt the progression or prevent the onset of this disorder.

In accordance with one embodiment of the present invention, treated and untreated mice of sufficiently advanced age (e.g., between 6–18 months of age) are compared in terms of brain activity. More particularly, in accordance with the invention, mice containing one or more genes known to cause or to increase the risk of Alzheimer's disease are treated for a designated time during the course of their relatively short lives, while another group of genetically comparable mice (studied previously or in random order) are followed for the same age interval in the absence of treatment or with placebo treatment only. The number of mice in each group is comparable and sufficient to detect statistically significant effects of treatment on an indicator of Alzheimer's disease progression. Potential treatments include, but are not limited to, pharmaceutical compounds, dietary supplements, gene therapies, vaccines, and behavioral or environmental therapies. At the end of the treatment period, an imaging technique is used to measure activity (e.g., FDG uptake) in different regions of the brain. Measurements of brain activity in the posterior cingulate cortex in older untreated animals may be compared to that in untreated younger animals to characterize the extent of Alzheimer's disease progression in the absence of treatment. Further, measurements of brain activity in older treated animals may be compared to that in untreated younger animals to characterize the extent of Alzheimer's disease progression following treatment. Moreover, posterior cingulate activity in older treated animals may be compared to that in older untreated animals to characterize the effects of treatment on Alzheimer's disease progression. In accordance with a preferred embodiment of the present invention, if older treated mice exhibit a higher level of brain activity in the posterior cingulate region than do older untreated mice, then a potentially efficacious treatment for Alzheimer's disease is identified.

One technique to characterize the age-related reductions in posterior cingulate activity is known as "FDG autoradiography." Using this technique, a radioactive form of the compound FDG is injected into an abdominal region of the mouse known as the peritoneum in an extremely small ("tracer") dose. After a short period of time (e.g., about 45 minutes), the mouse is sacrificed, the brain is extracted and frozen, and the brain is then cut into extremely thin sections. The sections are mounted onto slides and exposed to film in order to develop images of FDG uptake. After the posterior cingulate cortex and other brain regions are identified by a person who is unaware of the animal's treatment status, measurements in these regions are recorded and normalized for the variation in absolute brain measurements. Reductions in posterior cingulate FDG uptake in older untreated transgenic mice (in comparison with aged non-transgenic mice or young transgenic mice) provide an indicator of Alzheimer's disease. An attenuation in posterior cingulate FDG uptake reductions in older treated mice (in comparison with the untreated mice) is an indicator of treatment efficacy, that is, a promising treatment of Alzheimer's disease in humans. A treatment which reduces (or reverses) the decline in posterior cingulate FDG uptake, and is thought to be safe and tolerable, would be considered a promising candidate for clinical trials. A treatment which reduces the decline in posterior cingulate FDG uptake in addition to reducing the progression of other histopathological changes (e.g., plaque formation) would be considered an especially promising candidate for clinical trials.

In accordance with the invention, several functional brain imaging techniques and other methods may be suitable for characterizing the progression of Alzheimer's disease in transgenic mice and other promising animal models: those that produce relatively high-resolution (sharp) images reflecting the activity of neurons that project to the posterior cingulate cortex, the density of synapses in the posterior cingulate cortex, or the activity or density of surrounding ("glial") brain cells in this region. Imaging techniques may include, but are not limited to, certain autoradiographic and histochemical methods (which produce relatively sharp images, but require animal sacrifice) and positron emission tomography (PET), single emission computed tomography (SPECT), and magnetic resonance imaging (PET) systems especially designed for the study of small animals (which produce relatively blurry images, but permit researchers to use each animal as its own control as the living brain is studied on more than one occasion). Useful indicators of the processes noted above may include, but are not limited to, to markers of cerebral metabolism, blood flow, blood volume, mitochondria activity (e.g., cytochrome oxidase activity), other markers of synaptic density or activity, and other neurotransmitter or nerve receptor measurements that could reflect such activities. Images may be analyzed using preselected regions-of-interest or using computer algorithms that stack brain sections into a three-dimensional volume, transform each brain into the same orientation, size, and shape, average functional images from different brains, and create statistical maps of significant reductions in regional brain activity in the presence or absence of treatment.

The method of the present invention provides an indicator of disease progression in animal models that has been shown to correspond with the course of Alzheimer's disease in cognitively normal persons at genetic risk for Alzheimer's disease and persons with Alzheimer's dementia. For this reason, it provides a useful way to study treatments designed to prevent Alzheimer's disease and also treatments to attenuate or reverse the progression of Alzheimer's dementia in humans. Furthermore, it provides an indicator of Alzheimer's disease progression independent of the histopathological features which may or may not be present in the laboratory animals and may or may not be necessary or sufficient to cause Alzheimer's disease.

To date, the invention, monitoring reductions in posterior cingulate activity, appears to provide the best way to follow the progress of Alzheimer's disease in the absence of symptoms: first, to screen promising treatments in laboratory animals; subsequently, to investigate the ability of treatments to prevent (or delay onset of) Alzheimer's disease in cognitively normal persons at genetic risk for Alzheimer's disease without having to wait many years to determine whether or when treated persons go on to develop symptoms.

BRIEF DESCRIPTION OF FIGURES

FIG. 3 demonstrates that the abnormal reduction in posterior cingulate activity in the transgenic mice is progressive.

DETAILED DESCRIPTION OF THE PREFERRED EMBODIMENTS

Figure 1:
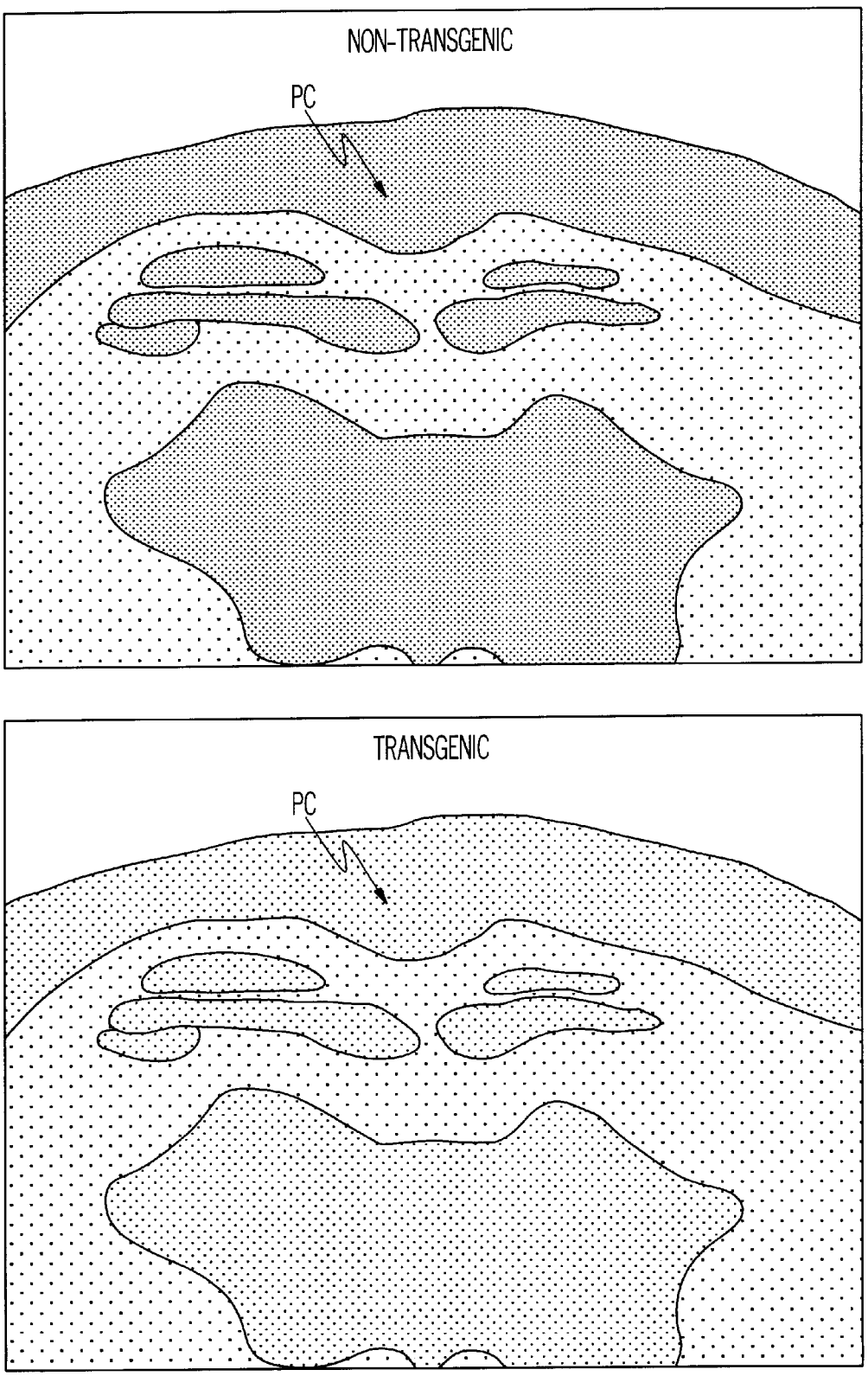
FIG. 1 shows autoradiographic sections of FDG uptake in the posterior cingulate cortex (PC) in a non-transgenic mouse and a transgenic mouse that contains a human Alzheimer's disease gene and develops amyloid plaques. As indicated in the lighter image, the transgenic mouse had reduced activity in the posterior cingulate cortex (and, to a lesser extent, in other brain regions)

The invention uses mice that are genetically modified to include a human gene that appears to cause or increase the risk of Alzheimer's disease and brain imaging techniques or other methods to characterize those regions of the brain that are identified in this invention as being preferentially affected during the onset of the disease, to test the effectiveness of various clinical treatments, including, for example, gene therapy, behavioral and environmental therapy, dietary supplements, and pharmaceutical compounds on the activity of these brain regions, and thereby select treatments with a high potential for arresting or reversing the progression of, delaying the onset of, or even preventing Alzheimer's disease altogether.

Functional brain imaging techniques can be used to provide information about the inner workings of the brain in non-human animal species. In the development of this invention, it was proposed that aged transgenic mice that exhibit some of the histopathological features of Alzheimer's disease would have a pattern of reductions in regional brain activity (e.g., reductions in regional FDG uptake) similar to those observed in persons affected by or at risk for Alzheimer's disease. In particular, it was postulated that these mice would have especially large reductions in the posterior cingulate cortex which, in contrast to parietal, temporal, and prefrontal regions, is relatively well developed in lower animal species, such as laboratory mice. A preferential and progressive reduction in FDG uptake (or other markers of brain activity) in the posterior cingulate cortex could help bridge the gap between studies of persons affected by or at risk for Alzheimer's disease and transgenic mice or other animal models of this disorder. The screening procedure could be used to help characterize the genetic factors, molecular events, and histopathological changes that are involved in the development of Alzheimer's disease (i.e., by assessing their relationship to the decline in posterior cingulate activity). More importantly, it could be used to screen treatments to halt the progression and prevent the onset of this terrible disorder. As previously suggested, this screening procedure could identify promising treatments for Alzheimer's disease in human beings (i.e., those treatments that attenuate or even reverse the decline in posterior cingulate activity), give chemists direction in the refinement or new design of promising pharmaceutical compounds, and give the pharmaceutical industry direction in selecting which treatments to test in potentially expensive and time-consuming clinical trials. The present invention confirms our hypothesis that transgenic mice have a characteristic and progressive reduction in posterior cingulate activity and supports the contention that changes in posterior cingulate activity provide an indicator of Alzheimer's disease progression.

Evaluation of the human brain shows that a progressive decline of glucose metabolism, a measure of the level of activity in the brain, correlates with the progressive decline of brain activity related to the onset and/or progression of Alzheimer's disease. For instance, PET studies have found that human patients with Alzheimer's dementia have progressive reductions in posterior cingulate, parietal, temporal, and prefrontal measurements of glucose metabolism (Reiman et al, *New Engl J Med*, 1996). The present inventor has found that changes in brain activity in mice genetically modified for Alzheimer's disease correlate to the above-mentioned changes in brain activity that have been found in humans with the disease.

In accordance with one embodiment of the present invention, transgenic mice having a gene modification that causes Alzheimer's disease are selected. Several strains of such mice are currently available. These strains are not identical and do not all exhibit the histopathological changes of the brain associated with the disease in humans. Thus, most mouse strains do not develop neurofibrillary tangles or neuritic plaques. It has recently been found that mice with an aberrant beta-amyloid precursor protein (APP) transgene develop neuritic plaques. These animals do not, however, develop neurofibrillary tangles, but nevertheless are the preferred transgenic mice in accordance with the present invention. These mice are available from Elan Pharmaceuticals, of 800 Gateway Boulevard, San Francisco, Calif. Since these mice develop visible brain lesions (plaques or tangles), they are useful to study in conjunction with brain activity levels to confirm the progression or otherwise of the disease. However, any now known or later developed genetically engineered mouse strains having characteristics useful in practicing the methods of the present invention can be used.

Useful mouse brain images may be developed by any of a number of techniques that provide the requisite degree of image resolution. Thus, while the following example of the invention uses FDG autoradiography (an imaging technique known to those of skill in the art), the invention is not limited to this technique. Other useful measuring/imaging techniques well known in the art include, but are not limited to, positron emission tomography (PET), single photon emission computed tomography (SPECT) of cerebral blood flow, perfusion-weighted magnetic resonance imaging (MRI) measurements of cerebral blood flow, and other imaging, autoradiographic, histochemical and staining procedures. For example, to the extent there is a desire to use PET to observe the level of activity in the brain, those skilled in the art are aware that a typical testing sequence includes performing a sequence of emission scans to obtain PET images of the brains of the test subjects, then using mathematical algorithms to align the sequential PET images, deform the images into the coordinates of a standard brain atlas, normalize the PET data, and generate statistical parametric maps of significant changes in brain activity among the test subjects (Reiman et al, *New Engl J Med*, 1996).

In accordance with one embodiment of the invention, a sample of transgenic mice of sufficient size to detect a significant alteration in posterior cingulate activity are subjected to a treatment protocol, either the administration of a drug to be tested, or gene therapy, or both. A second sample of untreated, genetically comparable transgenic mice, that is, mice having genetic modifications similar to the treated mice such that they are useful as a control group for later comparison of brain activity levels. Preferably, the untreated transgenic mice will have the same genetic modification as the treated transgenic mice, and may even be genetically identical. At the end of the treatment period, the mice are injected intraperitoneally with 1 microCi/100 g body weight of $^{14}$C-FDG, when FDG autoradiography is to be used. The length of the treatment period may vary according to the nature of the mice, the chosen treatment protocol, and/or the particular examination technique. For other techniques of brain examination, other appropriate treatments are available and known. The animals are each placed in a quiet, dimly lit environment for about 45 minutes. Thereafter, the mice are decapitated, and their brains are removed and stored at cryogenic temperatures, about minus 40 degrees centigrade. The frozen brain is then mounted onto the freezing stage of a precision cryostat and cut into contiguous coronal sections about 45 microns thick. These sections, and preferably only every third section, are then mounted onto slides that have been exposed to film for preparing autoradiographs. An exemplary autoradiograph is shown in FIG. 1.

Based on the autoradiographs, FDG uptake in each region of the brain can be computed. In accordance with one embodiment of the present invention, activity in the posterior cingulate region of the brain is most affected by the disease in mice and activity in thisarea is measured to determine treatment protocol efficacy.

In accordance with the invention, several comparisons are useful. For example, the posterior cingulate cortex in older untreated animals may be compared to that in untreated younger animals to characterize the extent of Alzheimer's disease progression in the absence of treatment. Untreated animals are those animals to which placebo or vehicle treatment is administered, or other control specimens not otherwise subjected to the treatment protocol. Further, measurements of brain activity in older treated animals may be compared to that in untreated younger animals to characterize the extent of Alzheimer's disease progression following treatment. Moreover, posterior cingulate activity in older treated animals may be compared to that in older untreated animals to characterize the effects of treatment on Alzheimer's disease progression. That is, a treatment with potential efficacy in halting, reversing, or otherwise treating Alzheimer's disease in humans will be associated with a higher level of posterior cingulate activity in the treated aged transgenic mice as compared to the posterior cingulate activity in the untreated aged transgenic mice. Thus, the present invention provides a range of potentially useful information in the identification and evaluation of treatments for Alzheimer's disease in humans, depending upon the comparisons selected and tested for.

EXAMPLE 1, below describes an embodiment of the invention using the FDG technique for imaging, and is intended to illustrate aspects the invention without limiting the invention, as set forth in the entirety of this document, including all the variations and modifications that will become apparent to one of skill in the art who has read this document.

EXAMPLE 1

Positron emission tomography (PET) studies find that persons with Alzheimer's disease have a characteristic pattern of reductions in fluorodeoxyglucose (FDG) uptake and that these reductions become more pronounced during the course of the illness. The largest reduction is in the posterior cingulate cortex, which is pathologically affected in Alzheimer's disease, becomes apparent prior to the onset of cognitive impairment in persons at genetic risk for the disorder, and might provide the most sensitive index of the pathological changes that herald the onset of dementia. Transgenic "PDAPP" mice who over express the V717F β-amyloid precursor protein (APP) progressively develop several pathological features of Alzheimer's disease, including amyloid deposits, neuritic plaques, synaptic loss, astrocytosis, and micro gliosis in the hippocampus and cortex. In this study, we used FDG autoradiography to compare aged transgenic mice homozygous for V717F APP with their non-transgenic, litter mates. We sought to test the hypothesis that the transgenic mice have preferentially reduced FDG uptake into the posterior cingulate cortex.

FDG autoradiographic data were acquired and analyzed in 11 aged transgenic mice (17.4±0.6 months of age) and 9 non-transgenic control mice (all 16.8 months of age) by personnel who were not informed about the animals' genotype, using methods previously described in detail. Each intact and unrestrained animal received an intraperitoneal (IP) injection of 1 $\mu$Ci/100 g body weight of $^{14}$C-FDG and was immediately placed in an individual cage in a quiet, dimly lighted room for 45 minutes. Immediately thereafter, the mouse was decapitated, its brain removed and stored at −40° C. The frozen brain was mounted onto the freezing stage of a precision cryostat and cut into contiguous 40 $\mu$m coronal sections. Every third section was mounted onto slides, which were exposed to Kodak EB-1 Film for preparation of the autoradiographs.

Optical densities in the FDG autoradiographs were analyzed using JAVA image-analysis software (Jandel Scientific Software, of 2591 Kerner Boulevard, San Rafael, Calif.). The images were placed on a DC-powered light box, captured with a high-resolution black-and-white video camera, and transmitted to a computer-mounted frame grabber for digitization. Each image was corrected for film background and camera-induced optical distortions by subtracting the background. A calibration curve was created based on the absolute gray levels of the $^{14}$C standards for FDG. Subsequent densitometric measures taken from brain images were then automatically expressed in terms of isotope incorporation ($\mu$Ci/g) for FDG update (Gonzalez-Lima, et al, 1993).

Seventy-one neuroanatomical regions of interest were identified in each animal using sections adjacent to the FDG images that were stained using cytochrome oxidase immunohistochemistry. Measurements of FDG uptake in each brain region were computed as the average of at least three readings. To investigate regions of the brain preferentially affected or spared in the transgenic mice independent of the variation in absolute measurements, regional data were normalized to a whole brain value of 1000 $\mu$Ci/g using the mean activity in all of the regions except the optic tract.

In comparison with the non-transgenic mice, the aged transgenic mice had a significant reduction in whole brain FDG uptake (1094±234 $\mu$Ci/g versus 739±257, $\mu$Ci/g, p=0.91) and since the transgenic mice continued to exhibit a significant reduction in whole brain-to-optic tract ratios (2.62±0.46 versus 5.47±2.96, p=0.0057), the reduction in whole brain FDG update appears to be at least partly related to a reduction in whole brain glucose metabolism.

Figure 2:
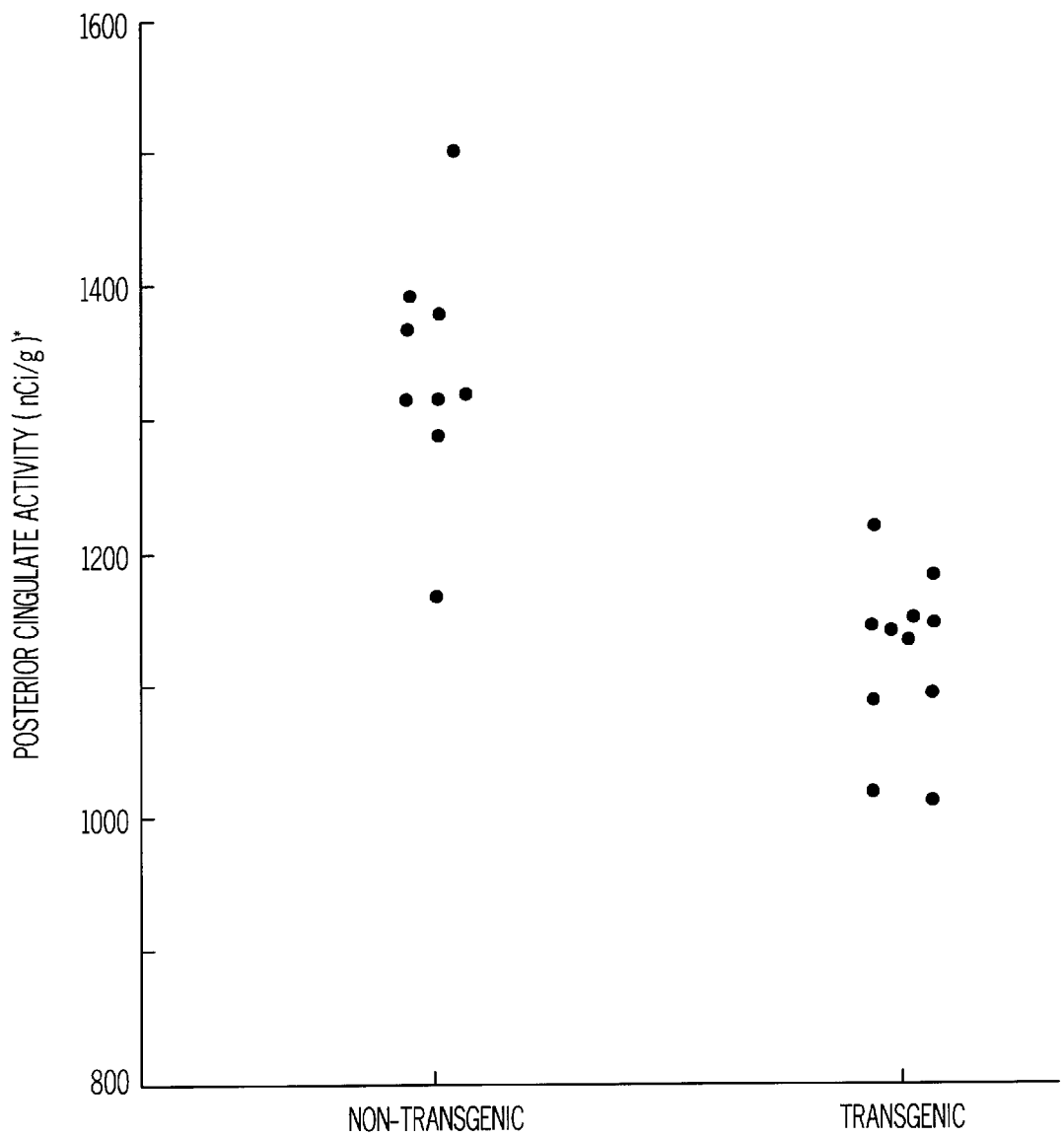
FIG. 2 is a graph depicting posterior cingulate FDG uptake in aged non-transgenic and transgenic mice (after adjusting each brain image for the variation in whole brain measurements) based on the results of EXAMPLE 1, below. Like persons affected by or at risk for Alzheimer's disease, the aged transgenic mice had significantly lower activity in the posterior cingulate cortex.

After normalizing the data for the variation in whole brain measurements, the aged transgenic mice had reduced FDG uptake in the posterior cingulate cortex (illustrated in FIG. 2), subiculum, presubiculum, and lateral septum, as well as the dorsomedial, centromedial, centrolateral, paraventricular, and lateral posterior thalamic nuclei (p<0.05, two-tailed t-tests, uncorrected for multiple comparisons (See Table 1 below)). As occurs in persons with Alzheimer's disease, the largest reduction was in the posterior cingulate cortex (the only reduction that remained significant following Bonferroni correction for multiple comparisons). Since the transgenic mice tended to be several days older than the non-transgenic mice (p=0.049), the reduction in posterior cingulate FDG uptake was confirmed after controlling for age (p=0.000018).

After normalizing the data for the variation in whole brain measurements, the aged transgenic mice had significantly greater FDG uptake (i.e., relatively spared FDG uptake) in visual area 18, rostral striatum, cerebellar vermis lobules 1–6, anterior and posterior parietal cortex (sensorimotor cortex), the molecular layer of hippocampal field CA1, the dorsal anterior pretectal area, the ventral tegmental area, and the optic tract. The greatest increase was in the visual area (the only increase that remained significant after Bonferroni correction for multiple comparisons). The preferential sparing of FDG uptake in visual cortex, sensorimotor cortex, brain stem, cerebellum, and white matter in the aged transgenic mice are consistent with that found in persons with Alzheimer's disease. Indeed, visual cortex appears to be the cortical region least affected in both the aged transgenic mice and persons with Alzheimer's disease.

In both persons with Alzheimer's disease and the transgenic mice, reductions in FDG uptake could reflect a reduction in the activity or density of terminal neuronal fields which innervate the implicated regions (rather than the cell bodies that arise there), the activity of synaptic glial cells, or an impairment in glucose metabolism unrelated to local neuronal activity. (In relatively low-resolution PET studies of persons with Alzheimer's dementia, the findings could also be partly attributable to the combined effects of atrophy and partial-volume averaging.) If the reductions reflect decreased activity of afferents to the posterior cingulate cortex and the other implicated regions, it should be possible to delineate the responsible projections in the transgenic mice using neural tract tracing methods or experimental lesions. Interestingly, while neuropathological changes appear to develop earliest and most extensively in hippocampus of persons with Alzheimer's disease, most PET studies have not detected reductions in hippocampal glucose metabolism. Similarly, while neuropathological changes appear to develop earliest and most extensively in the entorhinal cortex and dentate gyrus of the hippocampus, this study did not detect reduced FDG uptake in these regions; instead, it found reduced FDG uptake in regions of the hippocampal formation that receive projections from the entorhinal cortex and dentate gyrus (including the subiculum and presubiculum). Using brain imaging techniques in transgenic mice, it may now be possible to establish the relationship between alterations in neuropathology and brain function.

This study demonstrates the usefulness of the invention and the feasibility of using FDG autoradiography brain imaging methods to help bridge the gap between studies of Alzheimer's disease in human beings and genetically altered mice. It confirms that transgenic mice with age-dependent reductions in posterior cingulate activity could be used to track the progression of Alzheimer's disease, help elucidate its pathogenesis, and preclinically screen treatments to halt or reverse the progression and prevent the onset of this common and devastating disorder. It should be understood, however, that the methods herein described as being useful in the identification and measurement of activity in various regions of the brain are not exclusive; indeed, any now known or later-developed methods capable of achieving the results contemplated by the present invention are suitable for use in accordance with the present invention.

TABLE 1

FDG Uptake, Normalized to a Whole Brain Value of 1000 $\mu$Ci/g (Mean ± SD)

| Region | Transgenics (N = 11) | Controls (N = 9) | P-Value* |
|---|---|---|---|
| Posterior Cingulate (Pcg) | 1118 ± 63 | 1337 ± 90 | 0.0000055 |
| Retrosplenial Area (Rs) | 1108 ± 174 | 1253 ± 132 | 0.053 |
| Anterior Cingulate (Acg) | 1070 ± 133 | 1132 ± 143 | 0.32 |
| Parietal Cortex 1 (Par1) | 1302 ± 146 | 1222 ± 110 | 0.19 |
| Parietal Cortex 2 (Par2) | 1142 ± 172 | 1138 ± 119 | 0.96 |
| Parietal Cortex, Anterior (Apar) | 1361 ± 114 | 1176 ± 96 | 0.0011 |
| Parietal Cortex, Posterior (Ppar) | 1409 ± 146 | 1184 ± 127 | 0.019 |
| Frontal Cortex, Lateral (LFr) | 1246 ± 181 | 1117 ± 86 | 0.066 |
| Frontal Cortex, Medial (MFr) | 941 ± 112 | 990 ± 54 | 0.24 |
| Frontal Cortex, Sulcal (SFr) | 1255 ± 183 | 1255 ± 202 | 1.00 |
| Optic Tract (ot) | 395 ± 74 | 244 ± 135 | 0.0054 |
| Visual Cortex, Area 17 (A17) | 1208 ± 113 | 1122 ± 125 | 0.12 |
| Visual Cortex, Area 18 (A18) | 1333 ± 102 | 1081 ± 126 | 0.00011 |
| Visual Cortex, Area 18a (A18a) | 920 ± 119 | 1047 ± 173 | 0.067 |
| Auditory Cortex (Aud) | 1041 ± 126 | 1175 ± 219 | 0.10 |
| Hippocampal Field CA1 (CM) | 935 ± 90 | 973 ± 200 | 0.58 |
| Molecular Layer of CA1 (Mol) | 1044 ± 111 | 941 ± 57 | 0.021 |
| Hippocampal Field CA2 (C1) | 860 ± 43 | 917 ± 143 | 0.23 |
| Hippocampal Field CA3 (CA3) | 809 ± 84 | 848 ± 143 | 0.45 |
| Dentate Gyrus (DG) | 934 ± 97 | 888 ± 73 | 0.25 |
| Entorhinal Cortex (Ent) | 732 ± 35 | 719 ± 151 | 0.78 |
| Perirhinal Cortex (Per) | 850 ± 185 | 882 ± 122 | 0.66 |
| Subiculum (Sub) | 916 ± 41 | 1062 ± 113 | 0.00086 |
| Presubiculum (Psub) | 933 ± 65 | 1047 ± 155 | 0.039 |
| Septum, Lateral (LS) | 732 ± 81 | 825 ± 70 | 0.015 |
| Septum, Medial (MS) | 792 ± 102 | 870 ± 73 | 0.070 |
| Diagonal Band, Horizontal (HDB) | 913 ± 169 | 803 ± 102 | 0.030 |
| Diagonal Band, Vertical (VDB) | 851 ± 81 | 899 ± 150 | 0.37 |
| Amygdaloid Area, Anterior (AA) | 789 ± 140 | 812 ± 115 | 0.71 |
| Amygdaloid Nucleus, Central (CeA) | 572 ± 83 | 636 ± 193 | 0.33 |
| Amygdaloid Nucleus, Medial (MeA) | 584 ± 123 | 600 ± 161 | 0.80 |
| Amygdaloid Nucleus, Basolateral (BIA) | 824 ± 93 | 811 ± 93 | 0.76 |
| Accumbens Nucleus (Acb) | 772 ± 142 | 862 ± 60 | 0.095 |
| Striatum, Caudal (Cpc) | 812 ± 83 | 767 ± 124 | 0.34 |
| Striatum, Rostral (Cpr) | 1102 ± 83 | 1001 ± 56 | 0.0062 |
| Cerebellar Hemisphere (CbH) | 1167 ± 215 | 1090 ± 248 | 0.48 |
| Cerebellar Vermis, Lobules 1–6 (CbV1–6) | 1323 ± 144 | 1100 ± 137 | 0.0031 |
| Flocculus (Fl) | 1519 ± 293 | 1444 ± 222 | 0.54 |
| Thalamus, Anterior Ventral Nucleus (AV) | 1285 ± 246 | 1313 ± 83 | 0.75 |
| Thalamus, Centrolateral Nucleus (CL) | 1197 ± 87 | 1305 ± 118 | 0.030 |
| Thalamus, Contromedial Nucleus (CM) | 1051 ± 129 | 1187 ± 108 | 0.021 |
| Thalamus, Dorsomedial Nucleus (MD) | 1021 ± 83 | 1193 ± 112 | 0.00095 |
| Thalamus, Lateral Posterior Nucleus (LP) | 1120 ± 130 | 1291 ± 131 | 0.0091 |
| Thalamus, Parafascicular Nucleus (Pf) | 936 ± 59 | 958 ± 116 | 0.60 |
| Thalamus, Ventral Basal Nucleus, Lateral (VBL) | 1111 ± 179 | 1175 ± 96 | 0.35 |
| Thalamus, Ventral Basal Nucleus, Medial (VBM) | 1156 ± 166 | 1185 ± 105 | 0.66 |

TABLE 1-continued

FDG Uptake, Normalized to a Whole Brain Value of 1000 $\mu$Ci/g (Mean ± SD)

| Region | Transgenics (N = 11) | Controls (N = 9) | P-Value* |
|---|---|---|---|
| Thalamus, Paratenial Nucleus (Pt) | 936 ± 59 | 958 ± 116 | 0.60 |
| Thalamus, Paraventricular Nucleus (Pv) | 883 ± 144 | 989 ± 91 | 0.072 |
| Thalamus, Reticular Nucleus (Ret) | 989 ± 126 | 1076 ± 147 | 0.17 |
| Thalamus, Reuniens Nucleus (Re) | 1083 ± 151 | 1135 ± 68 | 0.35 |
| Lateral Geniculate Nucleus, Dorsal (LG) | 997 ± 129 | 1023 ± 54 | 0.58 |
| Zone Incerta (Zi) | 1031 ± 27 | 995 ± 113 | 0.71 |
| Subthalamic Nucleus (Sth) | 861 ± 202 | 832 ± 205 | 0.76 |
| Preoptic Area, Lateral (PoA) | 803 ± 200 | 732 ± 96 | 0.34 |
| Hypothalamus, Supraoptic Nucleus (SOH) | 690 ± 147 | 653 ± 124 | 0.56 |
| Hypothalamus, Ventromedial Nucleus (VMH) | 640 ± 143 | 678 ± 117 | 0.53 |
| Hypothalamus, Lateral (LH) | 960 ± 205 | 891 ± 97 | 0.36 |
| Hypothalamus, Paraventricular Nucleus (PVH) | 712 ± 111 | 684 ± 114 | 0.60 |
| Habenula, Lateral (Hb) | 1194 ± 114 | 1219 ± 121 | 0.65 |
| Ventral Tegmental Area (VTA) | 843 ± 187 | 678 ± 101 | 0.029 |
| Central Gray Area (CO) | 832 ± 89 | 838 ± 78 | 0.87 |
| Deep Mesencephalic Nucleus (DpMe) | 957 ± 147 | 882 ± 46 | 0.16 |
| Superior Colliculus, Deep Layers (SCDp) | 1101 ± 132 | 1036 ± 106 | 0.25 |
| Superior Colliculus, Superficial Layers (SCSu) | 1063 ± 171 | 1008 ± 96 | 0.40 |
| Red Nucleus (Red) | 957 ± 157 | 918 ± 59 | 0.49 |
| Nucleus of Cranial Nerve 3 (CN3) | 1173 ± 80 | 1081 ± 102 | 0.035 |
| Anterior Pretectal Area, Dorsal (APD) | 1354 ± 131 | 1187 ± 106 | 0.0062 |
| Anterior Pretectal Area, Ventral (APV) | 1294 ± 136 | 1204 ± 81 | 0.098 |
| Inferior Colliculus, Central (ICC) | 1078 ± 251 | 1165 ± 388 | 0.55 |
| Interpeduncular Nucleus (Ip) | 1314 ± 235 | 1117 ± 161 | 0.047 |
| Pontine Reticular Nucleus-Oral (PRO) | 870 ± 78 | 827 ± 87 | 0.26 |

*Two-Tailed T-Test

EXAMPLE 2

In order to determine the extent to which the reduction in posterior cingulate activity observed in aged transgenic mice (see EXAMPLE 1) is apparent prior to the accumulation of amyloid plaques (which first appear when these transgenic mice are about 6–9 months of age) or progresses with age (i.e., is an indicator of Alzheimer's disease progression), FDG autoradiography was subsequently used to study 10 young transgenic mice and 10 young non-transgenic mice (all 3.6 months of age).

Figure 3:
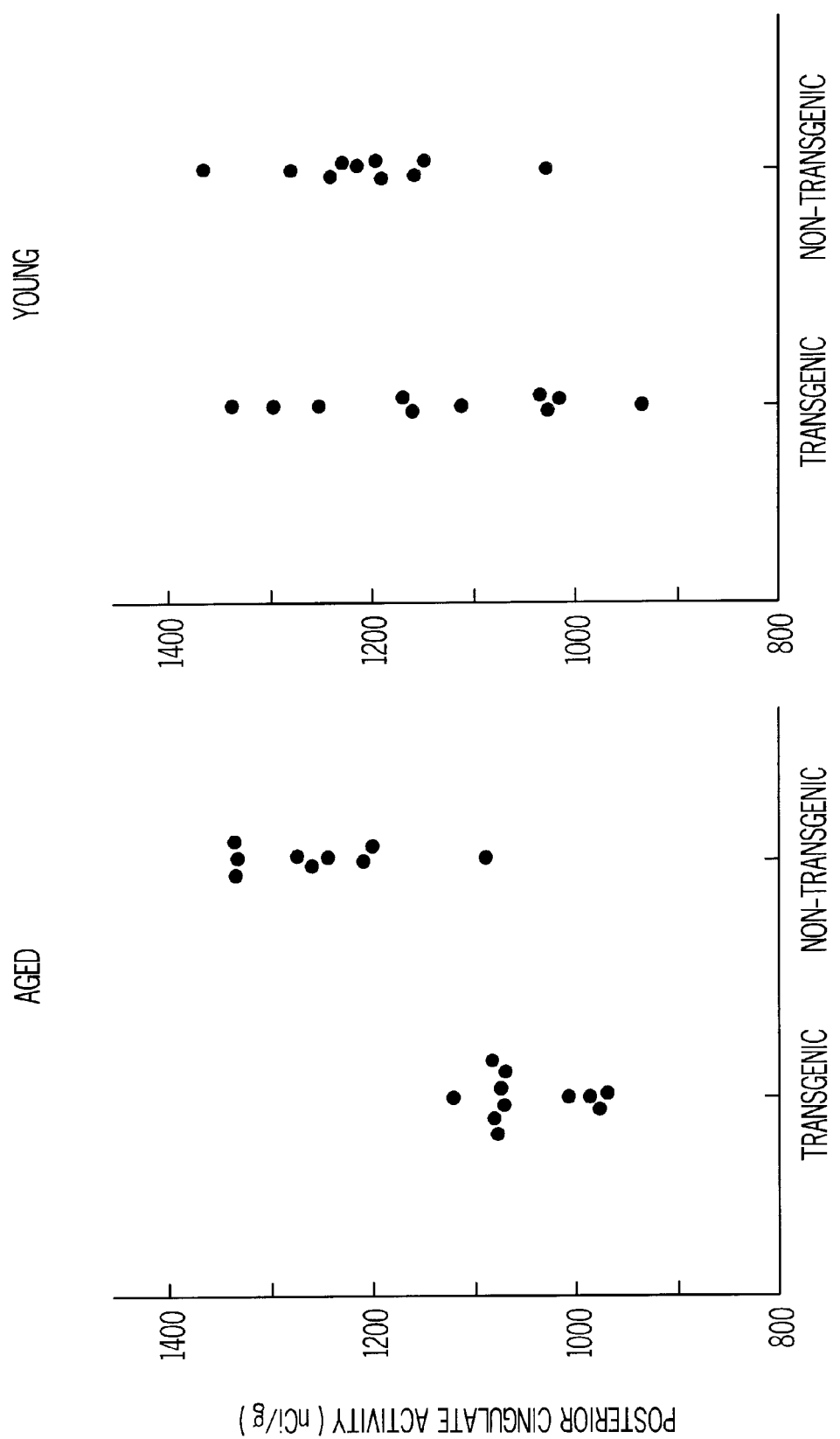
FIG. 3 is a graph depicting posterior cingulate FDG uptake in young non-transgenic and transgenic mice (after adjusting each brain image for the variation in whole brain measurements) based on the results of EXAMPLE 2, below.

After normalizing regional data for the variation in whole brain measurements using the mean activity of the 33 regions samples in every young and aged animal, the difference in posterior cingulate activity between the young transgenic and non-transgenic mice was not statistically significant (young TG: 1135±135 nCi/g; young NTG: 1204±89 nCi/g; two-tailed t-test, p=0.19), while posterior cingulate activity remained significantly lower in the aged transgenic mice than in the aged non-transgenic mice (aged TG: 1047±52 nCi/g; aged NTG: 1254±82 nCi/g; two-tailed t-test, p=0.0000019) (see FIG. 3). Indeed, there was a significant interaction between the transgenic and age conditions (i.e., the difference in posterior cingulate activity between the aged transgenic and non-transgenic mice was significantly greater than that between their young counterparts, two-factor analysis of variance [one-tailed t], p=0.013). These findings suggest that the abnormal reduction in posterior cingulate activity in the transgenic mice is progressive. Thus, the abnormal, age-dependent reduction in posterior cingulate activity in transgenic mice is believed to be an effective surrogate marker of Alzheimer's disease.

To the extent that age-dependent reductions in posterior cingulate activity track the progression of Alzheimer's disease, this measurement could be used in transgenic mice and other suitable laboratory animals to investigate how different genetic and non-genetic factors, neuropathological abnormalities, and molecular events contribute to disease progression. Moreover, it could be used to help screen candidate treatments (such as amyloid-β-peptide immunization, which was recently found to prevent the development of amyloid plaques, neuritic dystrophy, and astrogliosis in the same transgenic mouse strain). Treatments that promise to treat Alzheimer's disease in humans would be associated with higher level of brain activity in the posterior cingulate region of older treated mice than in older untreated mice. Among other things, this method may give the pharmaceutical industry direction in selecting which treatments to test in expensive and time-consuming clinical trials.

In sum, research studies of human patients clearly indicate a progressive decline of the level of activity in specific regions of the brain related to the onset and/or progression of Alzheimer's disease. Further, the present inventor has demonstrated that genetically modified mice having a gene that appears to cause and/or to increase the risk of Alzheimer's disease in humans exhibit similar declines in brain activity in analogous regions of the brain. This correlation between the changes in brain activity in transgenic mice and similar changes in brain activity in human patients with Alzheimer's disease promises to help bridge the gap between studies of Alzheimer's disease in human beings and laboratory animals. Thus, methods in accordance with this invention may be useful in efficiently and effectively identifying and evaluating treatments with the potential to halt the progression or prevent the onset of Alzheimer's disease.

The present invention has been shown and described in preferred form only, and by way of example, and many variations may be made in the invention that will still be comprised within its spirit. For example, although the foregoing discussion focuses on the measurement of activity in the posterior cingulate cortex, measurement of activity in other regions of the brain found to be preferentially affected in EXAMPLE 1 is possible in accordance with the present invention. Further, utilization of now known or later developed genetically engineered mouse strains having characteristics useful in practicing the methods of the present invention can be used. Moreover, myriad imaging and non-imaging techniques may be employed in accordance with the present invention. It is understood, therefore, that the invention is not limited to any specific form or embodiment except insofar as such limitations are included in the appended claims.

What is claimed is:

1. A method of evaluating treatments for Alzheimer's disease, the method comprising:
   (a) selecting a group of transgenic mice genetically modified for Alzheimer's disease;
   (b) treating the group of selected mice with a preselected treatment;
   (c) examining the brains of the mice to observe the level of activity in the posterior cingulate region of the brain; and
   (d) estimating the potential of the preselected treatment for the treatment of Alzheimer's disease based on the observed level of activity in the posterior cingulate region of the mouse brains.

2. The method according to claim 1, wherein said selecting step comprises selecting a group of transgenic mice having a gene that appears to cause or to increase the risk of Alzheimer's disease in humans.

3. The method according to claim 1, wherein said selecting step comprises selecting a group of transgenic mice having a beta-amyloid precursor protein (APP) transgene.

4. The method according to claim 1, wherein said selecting step comprises selecting a group of transgenic mice having a presenilin 1 transgene.

5. The method according to claim 1, wherein said selecting step comprises selecting a group of transgenic mice having a presenilin 2 transgene.

6. The method according to claim 1, wherein said selecting step comprises selecting a group of transgenic mice having an apolipoprotein E (APOE) ε4 transgene.

7. The method according to claim 1, wherein said treating step comprises treating a group of selected mice with pharmaceutical compounds.

8. The method according to claim 1, wherein said treating step comprises treating a group of selected mice with behavioral therapy.

9. The method according to claim 1, wherein said treating step comprises treating a group of selected mice with gene therapy.

10. The method according to claim 1, wherein said examining step comprises examining the brains of the mice using a process indicator.

11. The method according to claim 1, wherein said examining step comprises examining the brains of the mice using functional brain imaging techniques.

12. The method according to claim 1, wherein said examining step comprises examining the brains of the mice using FDG autoradiography and observing the amount of FDG uptake in the posterior cingulate region of the brains.

13. A method of evaluating treatments for Alzheimer's disease, the method comprising:
   (a) selecting a first group of transgenic mice genetically modified for Alzheimer's disease;
   (b) treating said first group of transgenic mice with a preselected treatment;
   (c) examining the brains of said first group of transgenic mice to observe the level of activity in the posterior cingulate region of the brain;
   (d) selecting a second group of untreated transgenic mice genetically comparable to said first group of transgenic mice;
   e) examining the brains of said second group of untreated transgenic mice to observe the level of activity in the posterior cingulate region of the brain;
   (f) comparing the observed level of activity in said first group of transgenic mice to the observed level of activity in said second group of untreated transgenic mice; and
   (g) estimating the potential of the preselected treatment for the treatment of Alzheimer's disease based on observed changes in activity in the posterior cingulate region of the brains of said first group of treated transgenic mice as compared to said second group of untreated transgenic mice.

14. The method according to claim 13, wherein said step of selecting a second group of untreated transgenic mice genetically comparable to said first group of transgenic mice comprises selecting a second group of untreated transgenic mice having the same genetic modification as said first group of transgenic mice.

15. The method according to claim 13, wherein said step of selecting a second group of untreated transgenic mice genetically comparable to said first group of transgenic mice comprises selecting a second group of untreated transgenic mice genetically identical to said first group of transgenic mice.

16. The method according to claim 13, wherein said examining steps (c) and (e) comprise examining the brains of said first group of transgenic mice using the same examination technique as in examining the brains of said second group of untreated transgenic mice.

17. The method according to claim 13, wherein said examining steps (c) and (e) comprise examining the brains of said first group of transgenic mice using a different examination technique as in examining the brains of said second group of untreated transgenic mice.

18. The method according to claim 13, wherein said examining steps (c) and (e) comprise examining the brains of the mice using FDG autoradiography and measuring the amount of FDG uptake in the posterior cingulate region of the brains.

19. The method according to claim 13, wherein said comparing step comprises comparing the observed level of activity in said first group of transgenic mice with the observed level of activity in said second group of untreated transgenic mice, wherein said second group has a comparable number of members as said first group.

20. A method of evaluating for Alzheimer's disease, the method comprising:

(a) selecting a group of transgenic mice genetically modified for Alzheimer's disease;

(b) treating the group of selected mice with a preselected treatment;

(c) examining the brains of the mice to observe activity in one or more regions of the brain; and (d) estimating the potential of the preselected treatment for the treatment of Alzheimer's disease based on observed changes in activity in the examined region or regions of the mice brains.

* * * * *

UNITED STATES PATENT AND TRADEMARK OFFICE
CERTIFICATE OF CORRECTION

PATENT NO. : 6,374,130 B1 Page 1 of 1
DATED : April 16, 2002
INVENTOR(S) : Reiman, Eric M.

It is certified that error appears in the above-identified patent and that said Letters Patent is hereby corrected as shown below:

Column 5,
Line 32, replace "(PET)" with -- (MRI) --.

Column 8,
Line 35, replace "thisarea" with -- this area --.

Column 11,
Line 24, replace "0.019" with -- 0.0019 --.
Line 30, replace "(CM)" with -- (CA1) --.
Line 32, replace "(C1)" with -- (CA2) --.

Column 12,
Line 26, replace "(CO)" with -- (CG) --.

Signed and Sealed this

Fifth Day of November, 2002

*Attest:*

*Attesting Officer*

JAMES E. ROGAN
*Director of the United States Patent and Trademark Office*